United States Patent
Ishii et al.

(10) Patent No.: US 8,337,364 B2
(45) Date of Patent: Dec. 25, 2012

(54) TRAINING SUPPORT SYSTEM AND TRAINING SUPPORT METHOD

(75) Inventors: Hiroshi Ishii, Kashiwa (JP); Kouichi Ohno, Tokyo (JP); Kazuo Yuge, Narashino (JP); Masahiro Katou, Asaka (JP); Sachihide Iwamoto, Fukuoka (JP); Makoto Hashizume, Fukuoka (JP); Hajime Kenmotsu, Fukuoka (JP); Shinichiro Takasugi, Fukuoka (JP)

(73) Assignee: Hitachi, Ltd., Tokyo (JP)

( * ) Notice: Subject to any disclaimer, the term of this patent is extended or adjusted under 35 U.S.C. 154(b) by 181 days.

(21) Appl. No.: 12/735,859

(22) PCT Filed: Mar. 3, 2009

(86) PCT No.: PCT/JP2009/055427
§ 371 (c)(1),
(2), (4) Date: Nov. 22, 2010

(87) PCT Pub. No.: WO2009/116622
PCT Pub. Date: Sep. 24, 2009

(65) Prior Publication Data
US 2011/0077127 A1    Mar. 31, 2011

(30) Foreign Application Priority Data
Mar. 19, 2008   (JP) ................................. 2008-072082

(51) Int. Cl.
*A63B 71/00* (2006.01)

(52) U.S. Cl. .................... 482/8; 482/1; 482/9; 482/901; 434/247

(58) Field of Classification Search ................. 482/1–9, 482/900–902; 434/236, 247
See application file for complete search history.

(56) References Cited

U.S. PATENT DOCUMENTS

| | | | |
|---|---|---|---|
| 4,569,518 A * | 2/1986 | Fulks | 482/5 |
| 7,470,216 B2 * | 12/2008 | Farinelli et al. | 482/3 |
| 2003/0108850 A1 * | 6/2003 | Murgia et al. | 434/236 |
| 2006/0098772 A1 * | 5/2006 | Reho et al. | 377/24.2 |

FOREIGN PATENT DOCUMENTS

| | | |
|---|---|---|
| JP | 2006-110046 | 4/2006 |
| JP | 2007-236557 | 9/2007 |

* cited by examiner

*Primary Examiner* — Glenn Richman
(74) *Attorney, Agent, or Firm* — Antonelli, Terry, Stout & Kraus, LLP.

(57) ABSTRACT

A training support system (S) allows an exerciser to practice training exercises safely and effectively with high motivation. The training support system (S) comprises a display means (4) which conducts display relating to training for the exerciser who uses a training machine (1) for muscle training, and a controller (3). The controller (3) allows dynamic display of reference motion and training motion on the display means (4) and variation of the display on the display means (4) according to the difference between the reference motion and the training motion.

4 Claims, 10 Drawing Sheets

FAILURE EXAMPLE 1

FAILURE EXAMPLE 2

FAILURE EXAMPLE 3

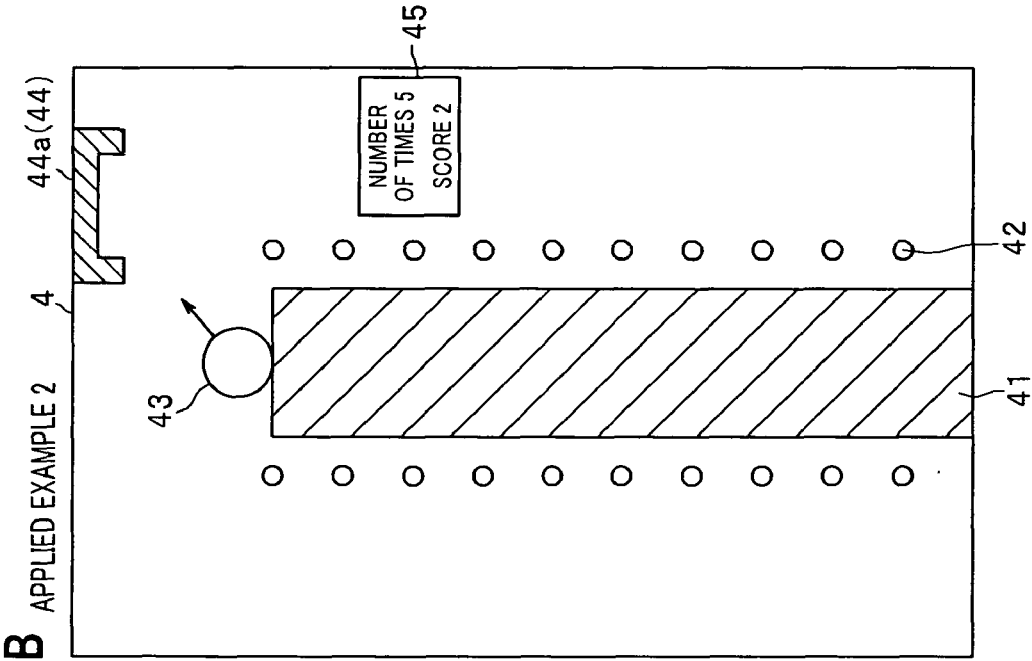
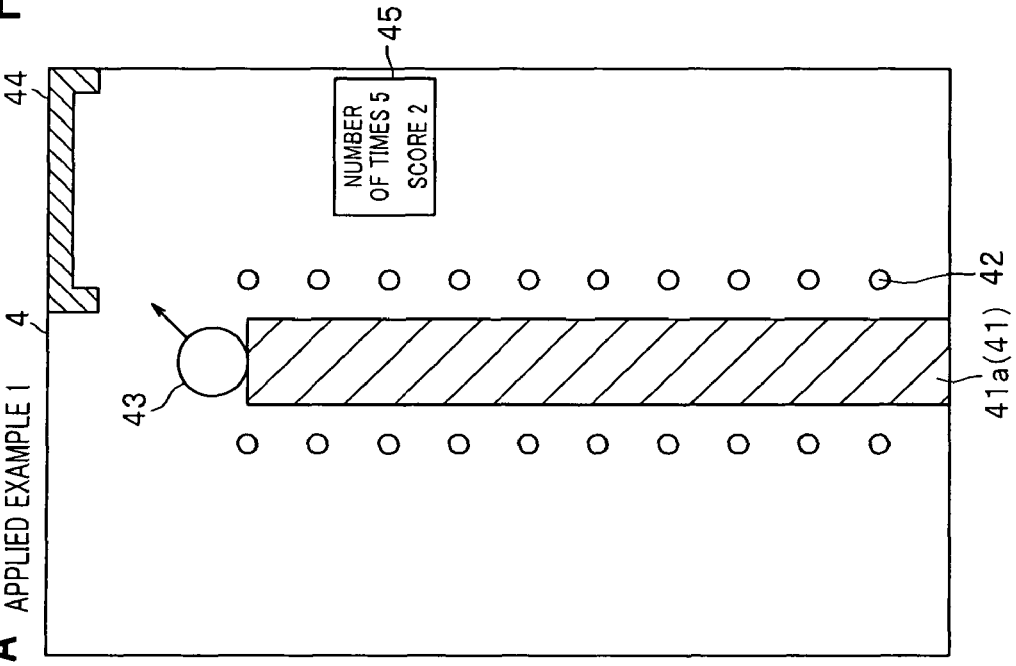

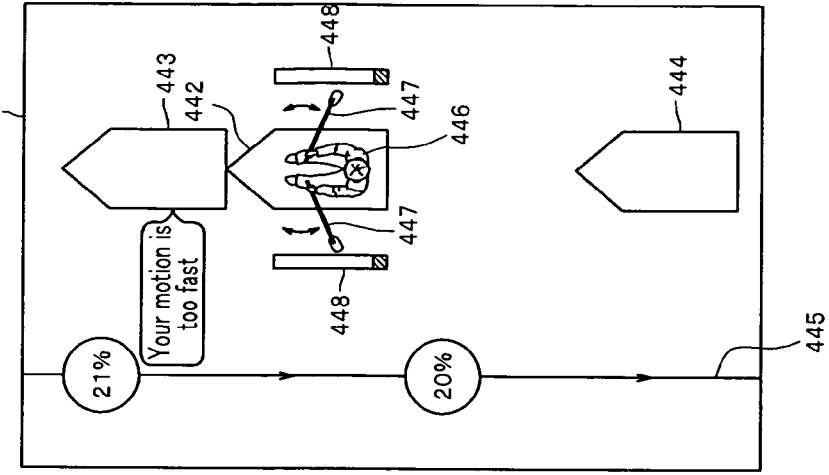
FIG.10A NORMAL EXAMPLE
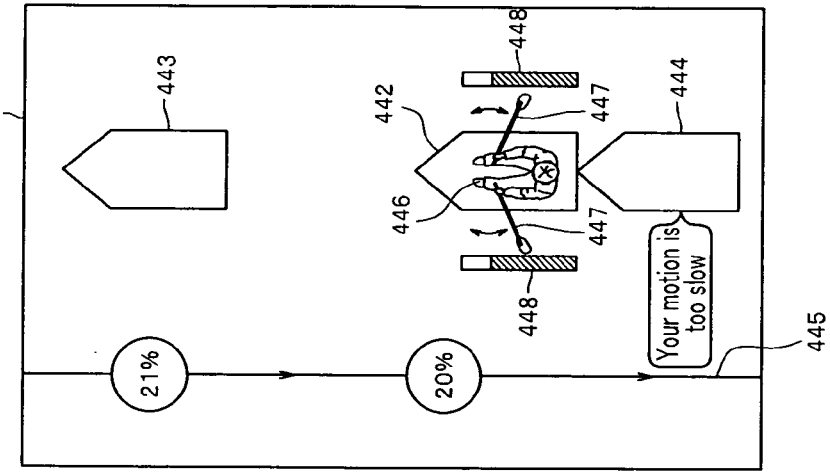
FIG.10B FAILURE EXAMPLE 1
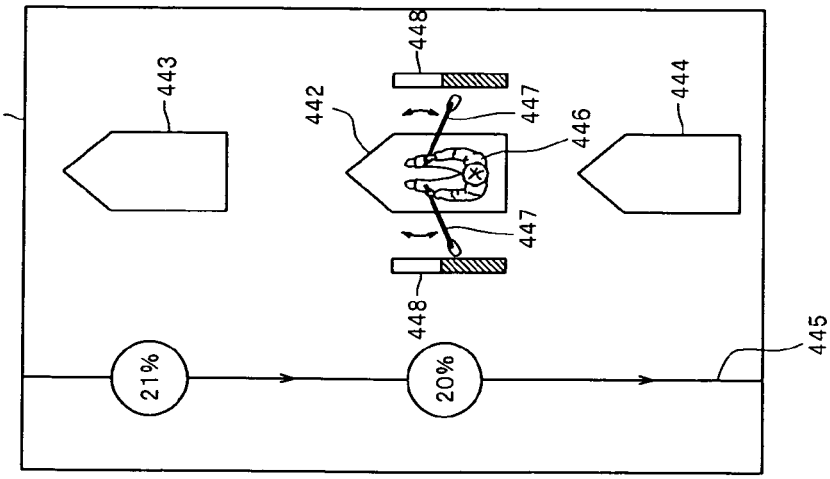
FIG.10C FAILURE EXAMPLE 2

TRAINING SUPPORT SYSTEM AND TRAINING SUPPORT METHOD

BACKGROUND OF THE INVENTION

1. Field of the Invention

The present invention relates to technology for supporting a training of an exerciser, in other words, technology for improving motivation of the exerciser for the training.

2. Description of the Related Art

In recent years, interest of the nation for health rises, various systems such as a system for preventing care have been enforced. And persons of advanced age who practices exercises with training machines are increasing. For example, for the training machine, there are a leg press machine to strengthen muscles of legs, a chest press machine to strengthen muscles of a chest and arms. In addition, for means which gives the exerciser a load in the training machine, there are a motor, board weights (metal plates), oil pressure and so on.

When the exerciser practices exercises with any kind of the training machine, it is important that the exerciser practices exercises with an appropriate load. In particular, it is not only training itself but also safety and effect of the training to be important for the person of advanced age. For example, technology of the training machine is disclosed in a patent publication (JP 2007-236557). The training machine gives the exerciser whose training motion is faster than standard motion a voice message "Your motion is too fast". In addition, the training machine gives the exerciser whose training motion is slower than standard motion a voice message "Your motion is too slow". In this way, the training machine corrects the training motion of the exerciser.

According to the above technology, the exerciser can be aware of whether the training motion ought to be fast or slow. However, the exerciser cannot judge (determine) easily how faster or slower the speed of the training motion should be.

In addition, for the instruction by the voice message, the exerciser may feel forced or obliged exercises, the exerciser may not be happy while practicing. As a result, there comes up a problem that the exerciser loses his or her motivation to continue the training.

This invention is intended to solve these problems. A purpose of this invention is to offer a training support system and a training support method which let the exerciser practice safe and effective training exercises with high motivation.

SUMMARY OF THE INVENTION

The present invention is a training support system comprising: a display means for displaying a training information for a exerciser who uses a training machine for training of muscles, and a controller, wherein the controller comprises; a reference motion setting section for setting a reference motion information which is given to the exerciser by using at least one of speed information, time information, displacement information relating to the training stored in a storage unit or input from an input means, a motion detection section for detecting training motion of the exerciser by using detection signals from a sensor which detects the training motion, a instruction output section for making an image corresponding to the reference motion and an image corresponding to the training motion, and instructing the display means to display them dynamically, the controller makes the display means change the display depending on the difference between the reference motion and the training motion.

Thus, this invention can let the exerciser practice safe and effective training exercises with high motivation.

BRIEF DESCRIPTION OF THE DRAWINGS

For a more complete understanding of the present invention and the advantages thereof, reference is now made to the following description taken in conjunction with the accompanying drawings wherein:

FIG. 7A, 7B are applied image examples displayed in the display means 4;

FIG. 10A is a normal image example, FIG. 10B, 10C are failure image examples.

DETAILED DESCRIPTION OF THE INVENTION

With reference to the drawings will be described embodiments of the invention in detail below.

Figure 1:
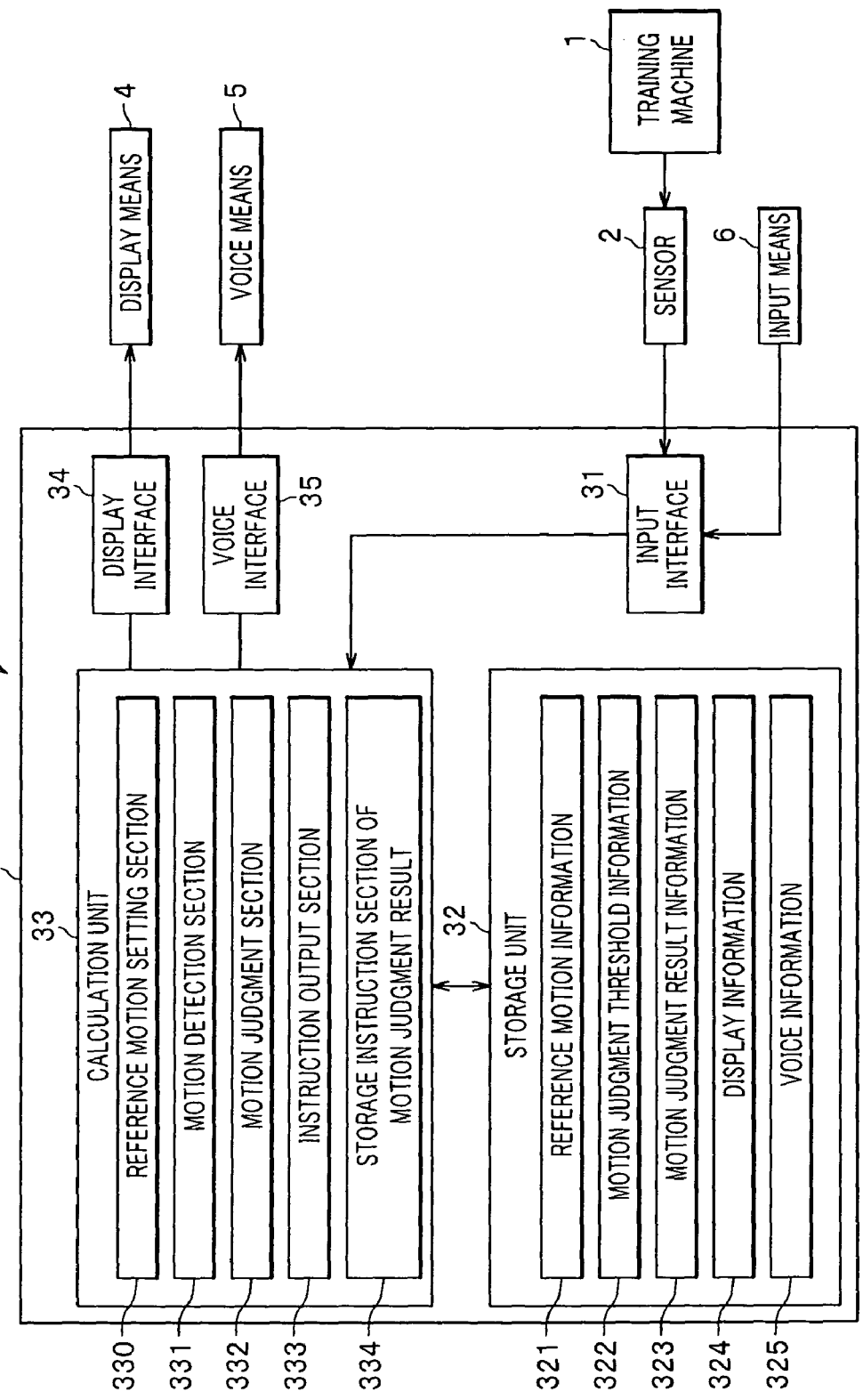
FIG. 1 is a figure showing a construction of the training support system according to the embodiment.

At first, the training support system according to the embodiment will be described with reference to FIG. 1. FIG. 1 is a figure showing a construction of the training support system S according to the embodiment. As shown in FIG. 1, the training support system S according to the embodiment comprises a training machine 1, a sensor 2, a controller 3, a display means 4, a voice means 5 and an input means 6.

The training machine 1 is a machine with which the exerciser practices training exercises. For means which gives the exerciser a load in the training machine 1, there are a motor, board weights, oil pressure. In addition, the training machine 1 may be a machine for strengthen any part such as arms, a chest, an abdomen, a back, legs of the exerciser. A concrete example of the training machine 1 will be described with reference to FIG. 2 later.

The sensor 2 is a sensor which detects motion of the exerciser with the training machine 1 and outputs detection signals, and is for example a sensor for detecting position, a sensor for detecting speed. A concrete example of the sensor 2 will be described with reference to FIG. 2 later.

The controller 3 comprises an input interface 31, a storage unit 32, a calculation unit 33, a display interface 34 and a voice interface 35, and may be realized by a PC (Personal Computer).

The input interface 31 inputs the detection signals from the sensor 2 and outputs the detection signals to the calculation unit 33, and may be composed of electronic circuits. In addition, the input interface 31 receives at least one of speed information, time information, displacement information relating to the training from the input means 6. The information is stored as reference motion information 321 in the storage unit 32 via the calculation unit 33. In addition, the information may be used directly by a reference motion setting section 330 of the calculation unit 33.

The storage unit 32 stores the reference motion information 321, a motion judgment threshold information 322, a motion judgment result information 323, a display information 324 and a voice information 325, and for example, is composed of ROM (Read Only Memory), HD (Hard Disk) and so on. In addition, the storage unit 32 stores several kinds of motion program (not shown in FIG. 1) for the calculation unit 33.

The reference motion information 321 is reference motion information of the training by the exerciser, and for example, motion speed information (or time which is necessary for one reciprocating motion) of legs at the training with the leg press machine (the training machine 1). In other words, the reference motion information 321 is at least speed information, time information, displacement information relating to the training. The information is used by the reference motion setting section 330 which sets reference motion information.

The motion judgment threshold information 322 is threshold information which is used when a motion judgment section 332 of the calculation unit 33 judges which the motion of the exerciser is success or not in comparison with the reference motion information 321, and for example, is information relating to a position or motion speed of a movable part of the training machine 1.

The motion judgment result information 323 is judgment result information about the motion of the exerciser, and for example, is success/failure information of each motion, or information of their sum.

The display information 324 is information displayed in the display means 4 relating to the training. Its detail will be described with reference to FIG. 3, 5, 9 later.

The voice information 325 is information relating to training being output from the voice means 5 to supplement information displayed in the display means 4. Its detail will be described later.

The calculation unit 33 comprises the reference motion setting section 330, a motion detection section 331, the motion judgment section 332, a instruction output section 333, and a storage instruction section of motion judgment result 334, and for example, is composed of CPU (Central Processing Unit) and RAM (Random Access Memory).

The reference motion setting section 330 sets the reference motion information by using the reference motion information 321 stored in the storage unit 32 (or by using information input from the input means 6). In addition, the reference motion represents motion of aim of an exerciser M in this embodiment.

The motion detection section 331 detects (calculates) motion of the exerciser by using information of the sensor 2 received from the input interface 31. For motion information of the exerciser, there are position information and motion speed information of the exerciser movable part in the training machine 1.

The motion judgment section 332 compares motion information of the exerciser detected by the motion detection section 331 and the reference motion information 321 stored in the storage unit 32, and concludes that motion of the exerciser is success if the difference is smaller than the motion judgment threshold information 322, concludes that motion of the exerciser is failure if the difference is not smaller than the motion judgment threshold information 322.

The instruction output section 333 instructs the display means 4 to display the reference motion as dynamic changeable figures by using the display interface 34 by using the reference motion information set by the reference motion setting section 330 ("by using the display interface 34" is omitted in the following). In addition, the instruction output section 333 instructs the display means 4 to display motion of the exerciser M detected by the motion detection section 331 (motion of a press part 13 in the training machine 1) as dynamic changeable figures. In addition, the instruction output section 333 instructs the display means 4 to display with the display information 324 depending on motion judgment result by the motion judgment section 332, and instructs the voice means 5 to output voice based on the voice information 325 by using the voice interface 35 ("by using the voice interface 35" is omitted in the following). In other words, the instruction output section 333 makes images corresponding to the reference motion and images corresponding to the training motion, and instructs the display means 4 to display them dynamically.

The storage instruction section of motion judgment result 334 instructs the storage unit 32 to store motion judgment result as motion judgment result information 323.

The display interface 34 instructs the display means 4 to display by an instruction from the instruction output section 333.

The voice interface 35 instructs the voice means 5 to output voice by an instruction from the instruction output section 333.

The display means 4 displays by an instruction from the display interface 34, and for example, is composed of LCD (Liquid Crystal Display).

Figure 2:
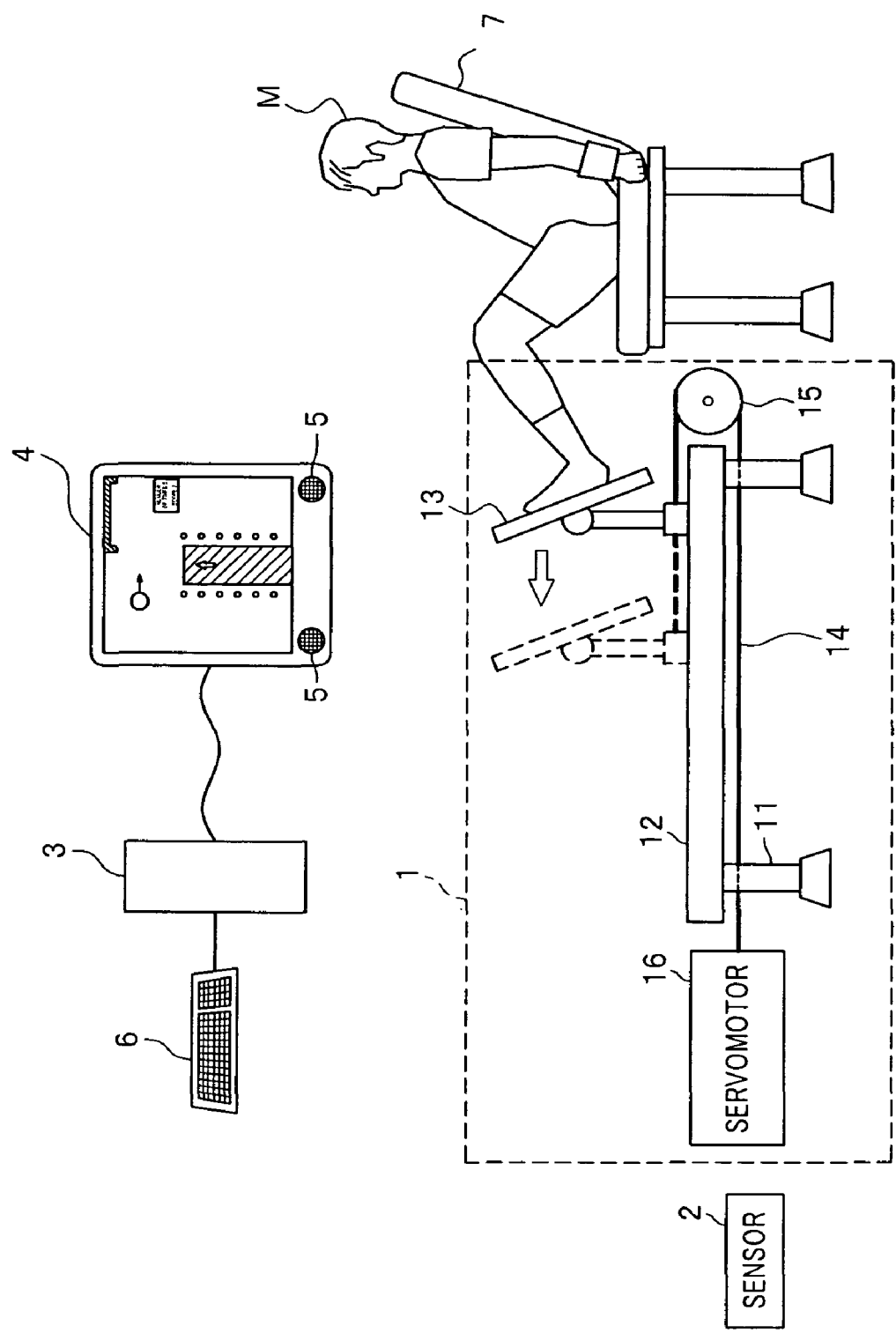
FIG. 2 is a figure showing a constitution of a concrete example of a training machine.

The voice means 5 outputs voice by an instruction from the voice interface 35, and for example, is composed of one of various speakers Next, a concrete example of the training machine 1 will be described. FIG. 2 is a figure showing a constitution of the concrete example of the training machine 1. As shown in FIG. 2, the training machine 1 is the leg press machine, and comprises a body 11, a rail 12, a press part 13, a wire 14, a pulley 15 and a servomotor 16.

In the training machine 1, the rail 12 is placed on the body 11, and the press part 13 slides on the rail 12. A bottom end of the press part 13 is connected to one end of the wire 14. Another end of the wire 14 is connected to the servomotor 16 through the pulley 15. For example, when there is an instruction from the controller 3, the servomotor 16 is actuated by the driving current which a driver (not shown) generates and pulls the wire 14 with the force depending on size of the driving current.

A chair 7 is placed in the right side of the training machine 1. The exerciser M sitting on the chair 7 practices his or her legs training of pushing the press part 13 with his or her legs against an output force of the servomotor 16. Then the sensor 2 detects motion of the servomotor 16 or motion of the wire 14 and transmits the detection signals to the input interface 31 of the controller 3. For example, for training contents, there is an exercise to repeat ten times bending and straightening his or her legs with a predetermined load.

Figure 3:
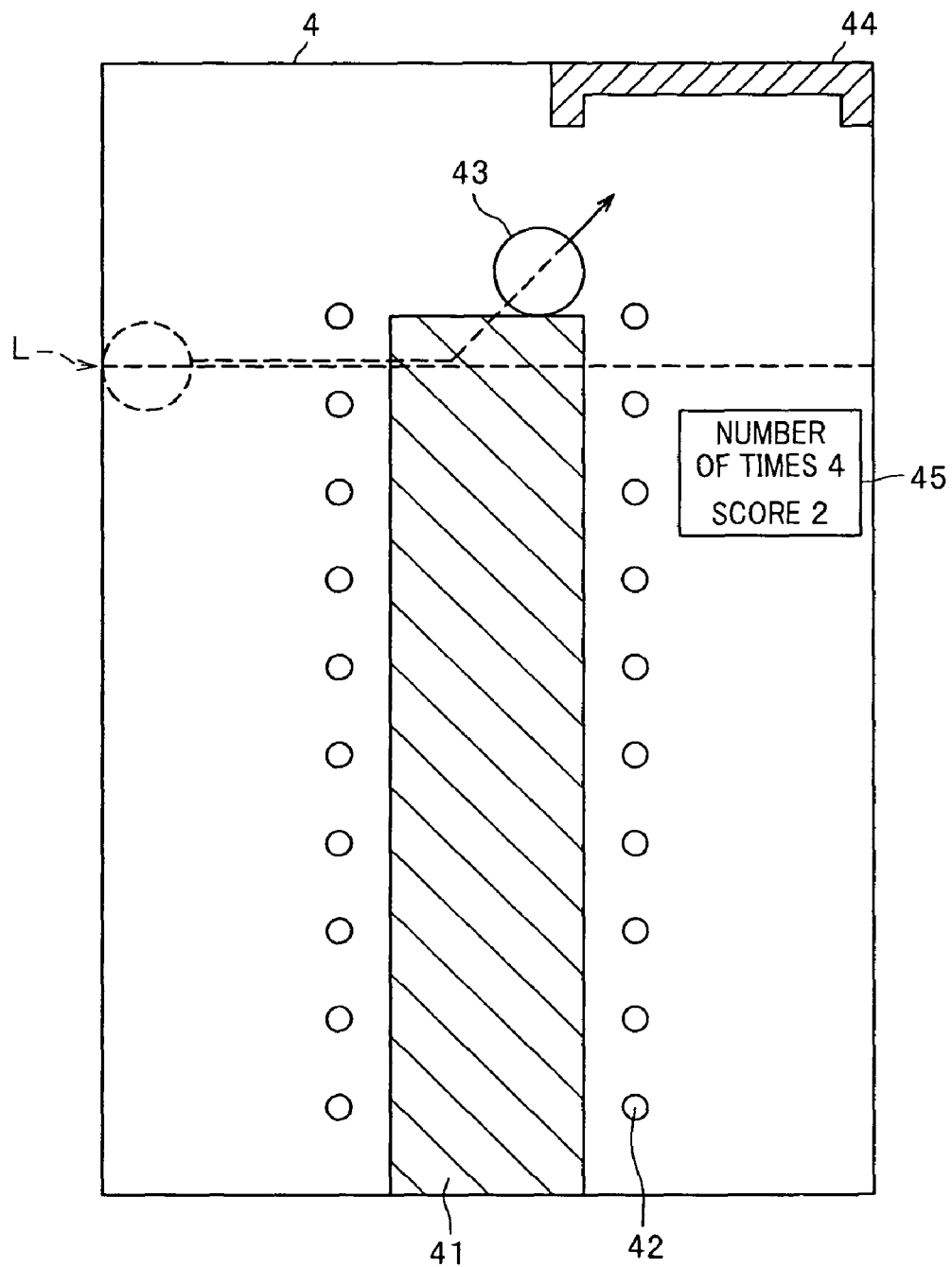
FIG. 3 is an image example 1 displayed in a display means 4.

Next, image examples displayed in the display means 4 during the training will be described. FIG. 3 is an image example 1 displayed in the display means 4. As shown in FIG. 3, a mobile bar 41 (image corresponding to the training motion), a guide display 42 (image corresponding to the reference motion), a ball 43 (image corresponding to the reference motion) and a goal 44 are displayed in the display means 4. In addition, there is a display area 45 in the display means 4.

The mobile bar 41 extends and contracts in the top and bottom direction, along with motion of the press part 13 in the training machine 1. Specifically, the mobile bar 41 moves toward the top in FIG. 3, when the exerciser M pushes the press part 13 with his or her legs and moves the press part 13 toward the left in FIG. 2. In addition, the mobile bar 41 moves toward the bottom in FIG. 3, when the exerciser M weakens the force of his or her legs and moves the press part 13 toward the right in FIG. 2.

The guide display 42 represents the reference motion which the reference motion setting section 330 sets by using the reference motion information 321. A top end part of the displayed 42 represents an ideal position for the top end part of the mobile bar 41. In addition, the guide display 42 may be displayed for a meter display.

The ball 43 moves to the right side from the left of the image (in the direction that is perpendicular to motion of the mobile bar 41). Line L in FIG. 3 represents motion line of the ball 43, but the Line L may not be displayed. When the mobile bar 41 moves the same way as the reference motion, the top end part of the guide display 42 collides with the ball 43. When the ball 43 collides with the top end part or a side part of the mobile bar 41, the ball 43 moves as if it is given dynamic force from the mobile bar 41. In other words, motion direction of the ball 43 changes.

The goal 44 is an area of the destinations to which the ball 43 collided by the top end of the mobile bar 41 which moves the same way as the reference motion moves.

The number of times and score are displayed in the display area 45. "NUMBER OF TIMES" represents the number of display times for guide of motion of legs by the guide display 42. "SCORE" represents the number of times for which the ball 43 goes into the goal 44. In other words, if the exerciser M does leg press motion in accordance with the guide display 42 (in other words, the difference between the reference motion and the training motion is small), the ball 43 surely collides with the top end of the mobile bar 41 and goes into the goal 44.

Figure 4:
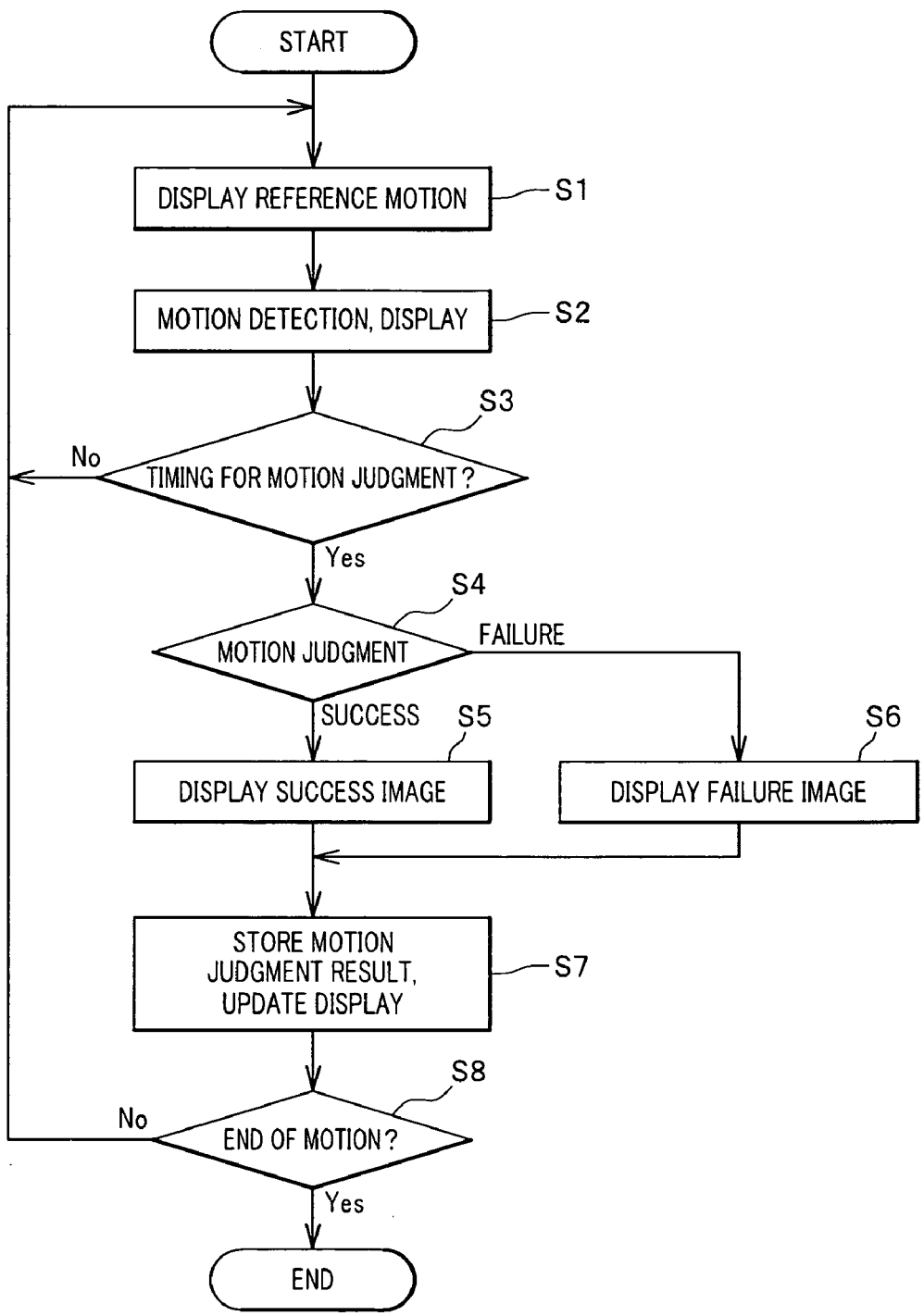
FIG. 4 is a flow chart showing processing of a controller 3 in the case that the image example 1 is displayed in the display means 4.

Next, processing of the controller 3 in the case that the image example 1 is displayed in the display means 4 will be described. FIG. 4 is a flow chart showing processing of controller 3 in the case that the image example 1 is displayed in the display means 4. Here, the case that the exerciser M practices training exercises of his or her legs for the number of predetermined times (for example, ten times) by using the training machine 1 shown in FIG. 2 is assumed.

The instruction output section 333 of the calculation unit 33 in the controller 3 instructs the display means 4 to display the reference motion (the guide display 42) (step S1). The exerciser M practices training exercises of his or her legs while looking at the reference motion (the guide display 42) in the display means 4.

The motion detection section 331 receives the detection signals from the input interface 31 and detects motion of the exerciser M (motion of the press part 13 in the training machine 1). The instruction output section 333 instructs the display means 4 to display motion of the mobile bar 41 by using the result of detection (step S2).

Next, the motion judgment section 332 judges whether it is a timing for motion judgment now (step S3). For example, the motion judgment section 332 judges the timing for motion judgment by detecting whether the mobile bar 41 moves toward the top and reaches the line L or not (in other words, by using a timing just before the turning point of the reciprocating motion). If it is not the timing for motion judgment (step S3→No), the processing returns to step S1.

If it is the timing for motion judgment (step S3→Yes), the motion judgment section 332 does the motion judgment (step S4). Specifically, the motion judgment section 332 compares motion information of the exerciser detected by the motion detection section 331 and the reference motion information 321, and concludes that motion of the exerciser is success if the difference is smaller than the motion judgment threshold information 322, concludes that motion of the exerciser is failure if the difference is not smaller than the motion judgment threshold information 322. In addition, for example, the motion judgment section 332 may judge whether the difference is smaller than the motion judgment threshold information 322 or not by judging whether the ball 43 collides with the top end having predetermined width of the mobile bar 41 or not.

If the result of the motion judgment is "success" (step S4→>"success"), the instruction output section 333 instructs the display means 4 to display the success image (step S5: its detail will be described with reference to FIG. 5).

If the result of the motion judgment is "failure" (step S4→"failure"), the instruction output section 333 instructs the display means 4 to display the failure image (step S6: its detail will be described with reference to FIG. 6).

After FIG. 5 or FIG. 6, the storage instruction section of motion judgment result 334 instructs the storage unit 32 to store motion judgment result in step S4 as the motion judgment result information 323 and instructs the display means 4 to update the display (step S7: its detail will be described with reference to FIG. 5)

Next, the motion detection section 331 judges whether motion of the training is over or not (step S8). The motion detection section 331 judges whether motion of the training is over or not, for example by judging whether detection signals from the input interface 31 changes or not, or by judging whether the number of motion times of the training reaches the predetermined number of times (for example, ten times) or not.

If motion of the training is not over (step S8→No), the processing returns to step S1. If motion of the training is over (step S8→Yes), the processing is over.

Next, an image example in the case that training motion is success will be described. FIG. 5A-5D are figures for describing image examples in the case that training motion is success. With order of FIG. 5A→5B→5C→5D, images of training motion in the display means 4 changes.

Figure 5A:
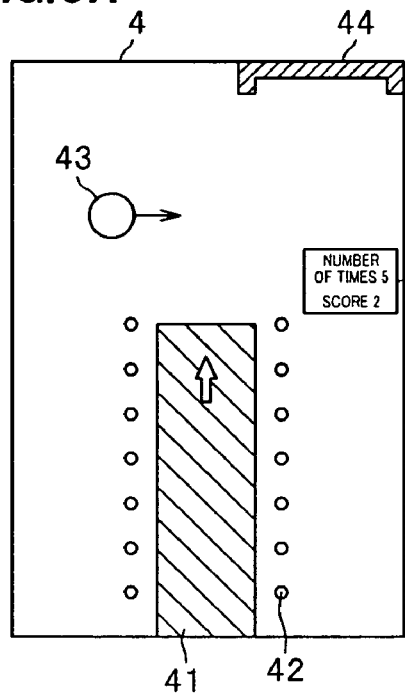
FIG. 5A-5D are figures for describing image examples in the case that the training motion is success.

FIG. 5A shows a scene that the exerciser M moves the press part 13 toward the left in FIG. 2 by pressing the press part 13 with his or her legs and shows a scene repeating step S1→step S2→step S3 "No"→step S1 of the flow chart in FIG. 4. FIG. 5A shows a halfway situation until the exerciser M extends completely his or her legs. At the time, a task given the exerciser M is to straighten his or her legs as indicated by motion of the guide display 42.

Figure 5B:
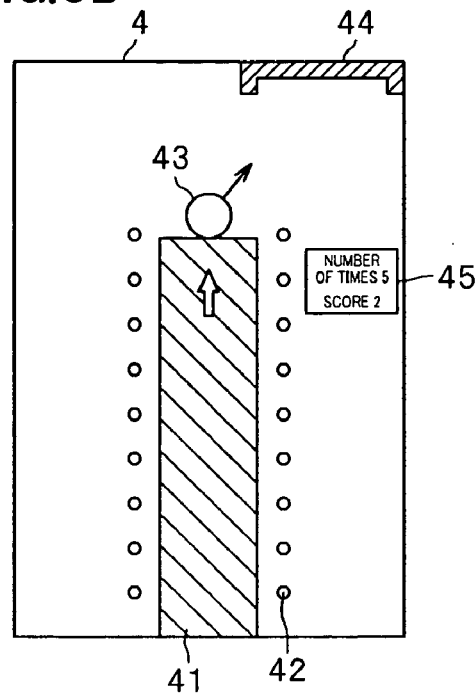

FIG. 5B shows a scene that the exerciser M moves the press part 13 toward the left in FIG. 2 more than the case indicated in FIG. 5A by pressing the press part 13 with his or her legs. At the time, "Yes" is selected in step S3 of the flow chart in FIG. 4. Here, because a difference between motion of the mobile bar 41 and display of the guide display 42 is smaller than the motion judgment threshold information 322, "success" is selected in step S4, display shown in FIG. 5C is done as the success image (pattern) (step S5).

Figure 5C:
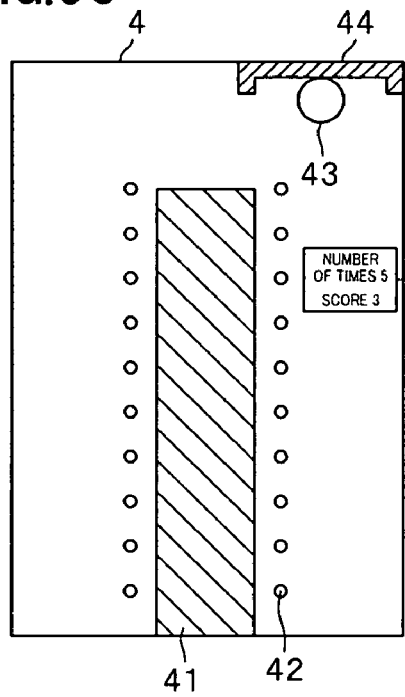

FIG. 5C shows the success image in which the ball 43 goes into the goal 44 (step S5). In addition, the storage instruction section of motion judgment result 334 instructs the storage unit 32 to store the result "success" of motion judgment in step S4 as the motion judgment result information 323 and changes the score in the display area 45 of the display means 4 from "2" to "3" by adding "1" to the score (step S7). In addition, the motion of the ball 43 in FIG. 5A naturally goes along with motion of the guide display 42. And if the exerciser M moves his or her legs the same way as motion of the guide display 42, the ball 43 surely collides with the top end of the mobile bar 41 and goes into the goal 44.

Figure 5D:
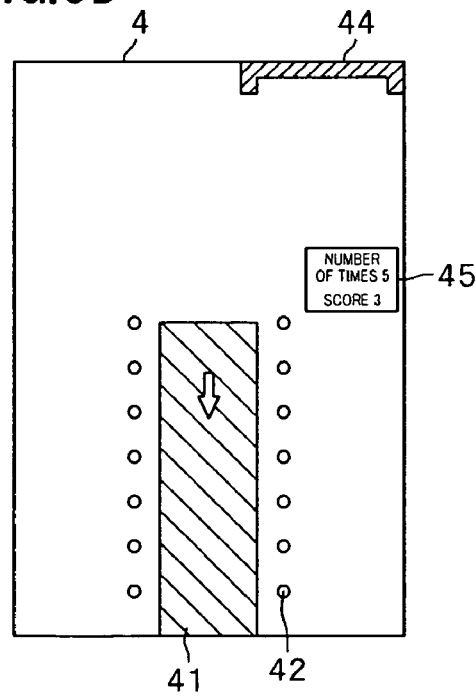
Figure 6A:
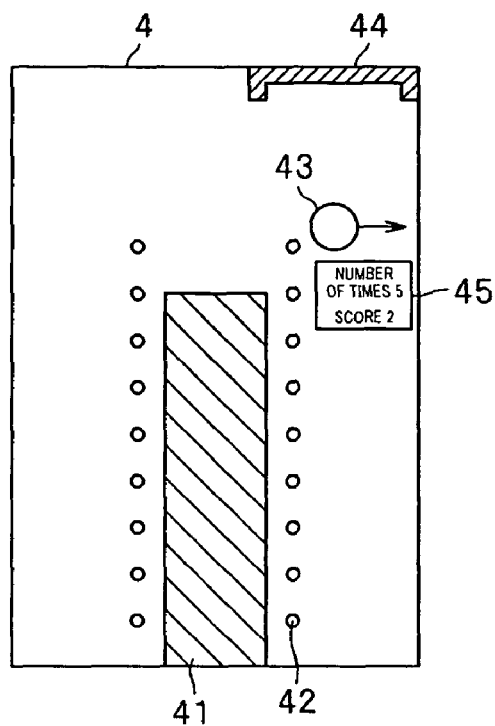
FIG. 6A-6C are figures for describing image examples in the case that training motion is failure.
Figure 6B:
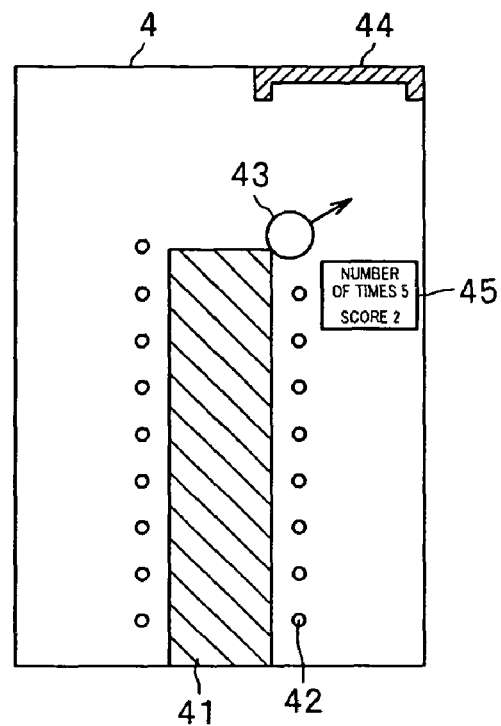
Figure 6C:
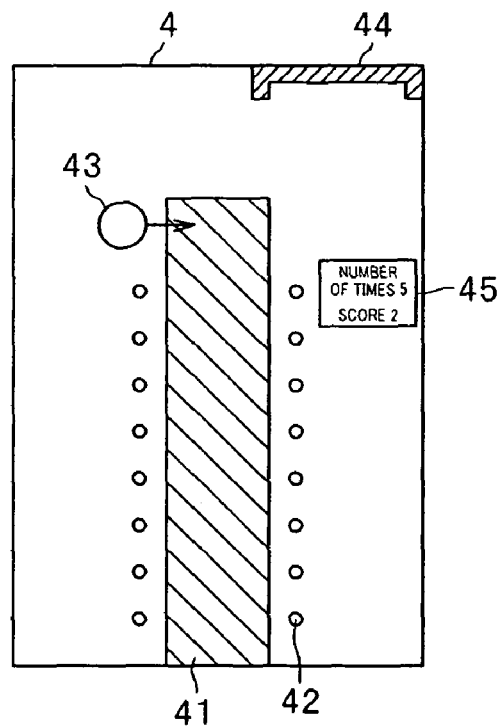

FIG. 5D shows an image in which the exerciser M moves the press part 13 toward the right in FIG. 2 more than the case indicated in FIG. 5C by weakening the force of his or her legs, and the mobile bar 41 moves toward the bottom in FIG. 3. In other words, after step S8 "No", step S1→4 step S2→step S3 "No"→step S1 is repeated Next, image examples in the case that training motion is failure will be described. FIG. 6A-6C are figures for describing image examples in the case that training motion is failure.

As shown in FIG. 6A, in a failure example 1, motion of the exerciser M is very slower than the reference motion. Therefore, the motion judgment section 332 compares motion information of the exerciser detected by the motion detection section 331 and the reference motion information 321, and concludes that motion of the exerciser is failure because the difference is not smaller than the motion judgment threshold information 322 (step S4→>"failure").

Therefore, the instruction output section 333 instructs the display means 4 to display the failure image (pattern) (step S6). In other words, the instruction output section 333 instructs the display means 4 to display an image in which the ball 43 goes straight toward the right, and doesn't go into the goal 44 as the failure image. In addition, the storage instruction section of motion judgment result 334 instructs the storage unit 32 to store the result "failure" of motion judgment in step S4 as the motion judgment result information 323 and doesn't change the score in the display area 45 of the display means 4 and keeps the score "2" (step S7).

As shown in FIG. 6B, in a failure example 2, motion of the exerciser M is slower than the reference motion. Therefore, the motion judgment section 332 compares motion information of exerciser detected by the motion detection section 331 and the reference motion information 321, and concludes that motion of the exerciser is failure because the difference is not smaller than the motion judgment threshold information 322 (step S4→>"failure").

Therefore, the instruction output section 333 instructs the display means 4 to display the failure image (step S6). In other words, the instruction output section 333 instructs the display means 4 to display an image in which the ball 43 touches the top end of the mobile bar 41 a little and advances to the direction of the top right corner, but doesn't go into the goal 44 as the failure image. In addition, the storage instruction section of motion judgment result 334 instructs the storage unit 32 to store the result "failure" of motion judgment in step S4 as the motion judgment result information 323 and doesn't change the score in the display area 45 of the display means 4 and keeps the score "2" (step S7).

As shown in FIG. 6C, in a failure example 3, motion of the exerciser M is very faster than the reference motion. Therefore, the motion judgment section 332 compares motion information of exerciser detected by the motion detection section 331 and the reference motion information 321, and concludes that motion of the exerciser is failure because the difference is not smaller than the motion judgment threshold information 322 (step S4→>"failure").

Therefore, the instruction output section 333 instructs the display means 4 to display the failure image (step S6). In other words, the instruction output section 333 instructs the display means 4 to display an image in which the ball 43 collides with the left side surface of the mobile bar 41 and bounces, and doesn't go into the goal 44 as the failure image. In addition, the storage instruction section of motion judgment result 334 instructs the storage unit 32 to store the result "failure" of motion judgment in step S4 as the motion judgment result information 323 and doesn't change the score in the display area 45 of the display means 4 and keeps the score "2" (step S7).

Thus, according to the training support system S, the controller 3 processes to make the ball 43 go into the goal 44 and to add the score in the display area 45 as display of the success image, if motion of the exerciser M is the same (or almost same) as the reference motion. In addition, the controller 3 processes not to make the ball 43 go into the goal 44 and not to add the score in the display area 45 as display of the success image, if motion of the exerciser M is not the same as the reference motion. Therefore, the exerciser M may practice training exercises with game sense, pleasure and high motivation, while performing safe and effective motion similar to the reference motion.

Next, applied image examples displayed in the display means 4 will be described. FIG. 7A-7B are applied image examples displayed in the display means 4. In addition, about the constitution same as the display image in FIG. 3, the same marks are given. And the explanation to repeat is omitted.

FIG. 7A is an applied image example 1. Width of the mobile bar 41a (41) is narrow. Therefore, a degree of difficulty to make the ball 43 go into the goal 44 increases. In other words, the training is set for the advanced. In this case, display of width of the mobile bar 41a should be narrow and a value of the motion judgment threshold information 322 should be set small (severe). In addition, likewise, the training may be set for a beginner by making the mobile bar 41 wide.

FIG. 7B is an applied image example 2. Width of the goal 44a (44) is narrow. Therefore, a degree of difficulty to make the ball 43 go into the goal 44 increases. In other words, the training is set for the advanced. In this case, display of width of the goal 44a should be narrow and a value of the motion judgment threshold information 322 should be set small (severe). In addition, likewise, the training may be set for a beginner by making the goal 44 wide.

In other words, the instruction output section 333 may change size and shape of display of the training motion of the exerciser M, the reference motion based on the reference motion information 321 stored in the storage unit 32, and their relation (for example the goal 44) in the display means 4, depending on the kind of the motion judgment threshold information 322. These setting may be done by the input means 6.

Figure 8:
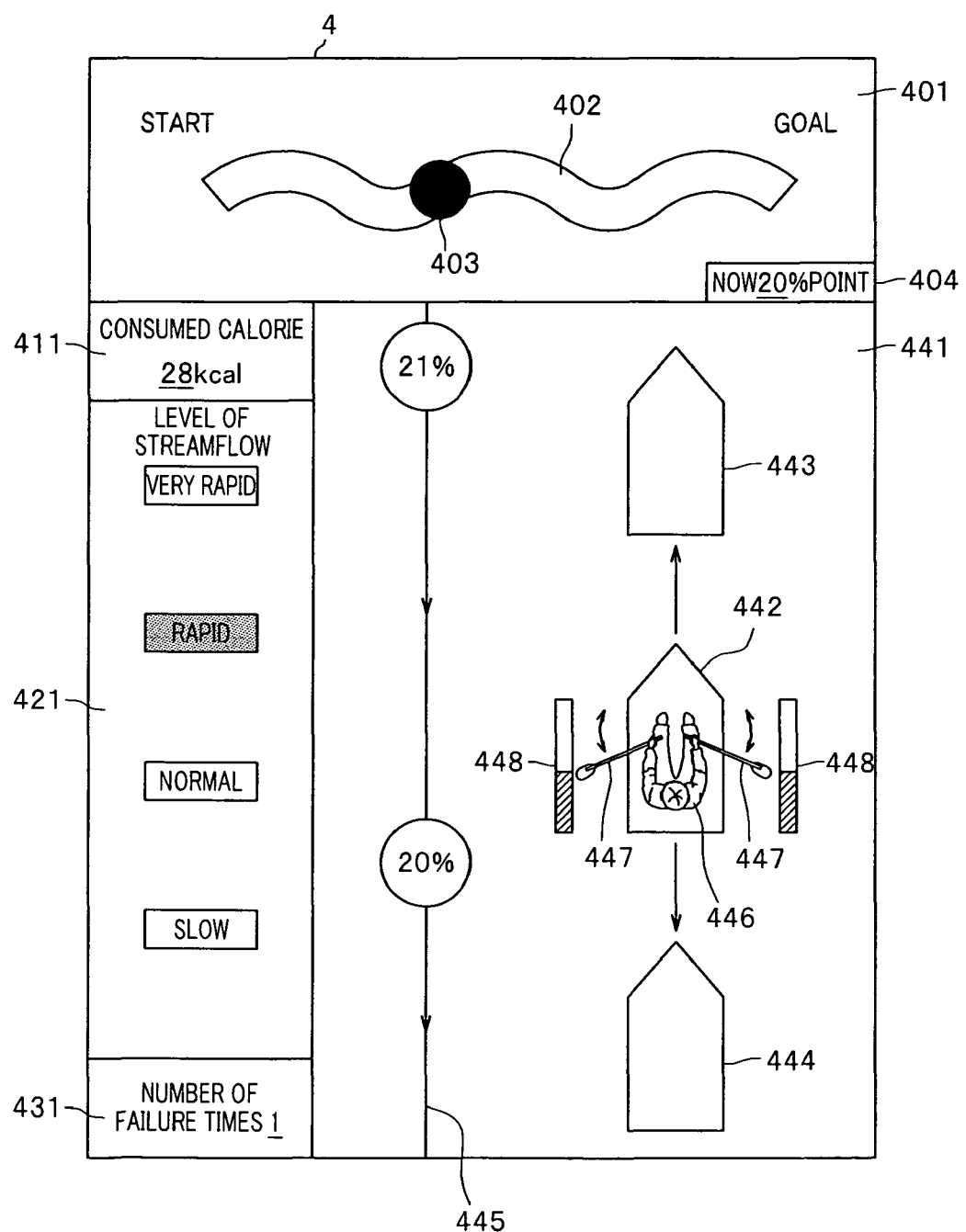
FIG. 8 an image example 2 displayed in the display means 4.

Next, FIG. 8 an image example 2 displayed in a display means 4. As shown in FIG. 8, a display area 401, a display area 411, a display area 421, a display area 431 and a display area 441 are displayed in the display means 4. In addition, their display information is stored as the display information 324 in the storage unit 32.

River 402 showing a process from a start of the training to a end of the training for a chart, a display 403 showing its progress degree (a point in the river 402) and a display 404 displaying the progress degree by percentage are displayed in the display area 401.

The number of current consumed calories is displayed in the display area 411.

For example, a level of streamflow is displayed for one of 4 steps "VERY RAPID", "RAPID", "NORMAL", "SLOW". Here, selected "RAPID" is displayed as example. In addition, the number of levels may be any (including one). In addition, the continuous number such as 0-100 may be set.

The number of failure times of motion is displayed in the display area 431.

An own ship 442 (image corresponding to the training motion), a guidance ship 443, a rescue ship 444, a milestones 445, a rower 446, an oars 447 (image corresponding to the training motion) and a meter indications 448 are displayed in the display area 441. In addition, the guidance ship 443, the rescue ship 444, the milestones 445 and the meter indications 448 are image corresponding to the reference motion and are set by the reference motion setting section 330 with the reference motion information 321. Here, the guidance ship 443 and the rescue ship 444 go ahead (to the top direction in FIG. 8) relatively with constant speed, and their absolute positions in the display area 441 are fixed.

The own ship 442 moves to top and bottom directions by motion of the exerciser M. Specifically, if motion of the exerciser M is the same as the reference motion, the position of the own ship 442 doesn't change. But, if motion of the exerciser M is faster than the reference motion, the own ship 442 moves toward the top. In addition, if motion of the exerciser M is slower than the reference motion, the own ship 442 moves toward the bottom. In other words, display in the display means 4 changes depending on the difference between the reference motion and the training motion. The oars 447 rowed by the rower 446 move while going along with motion of the exerciser M (motion of the press part 13 in the training machine 1). The reference motion (position) of training is displayed corresponding to outside end of the oars 447 in the meter indications 448. In other words, if motion of the exerciser M is the same as the reference motion, motion of the meter indications 448 is the same as motion of outside end of the oars 447. The milestones 445 represent positions in the river 402 and move toward the bottom with time progress.

Figure 9:
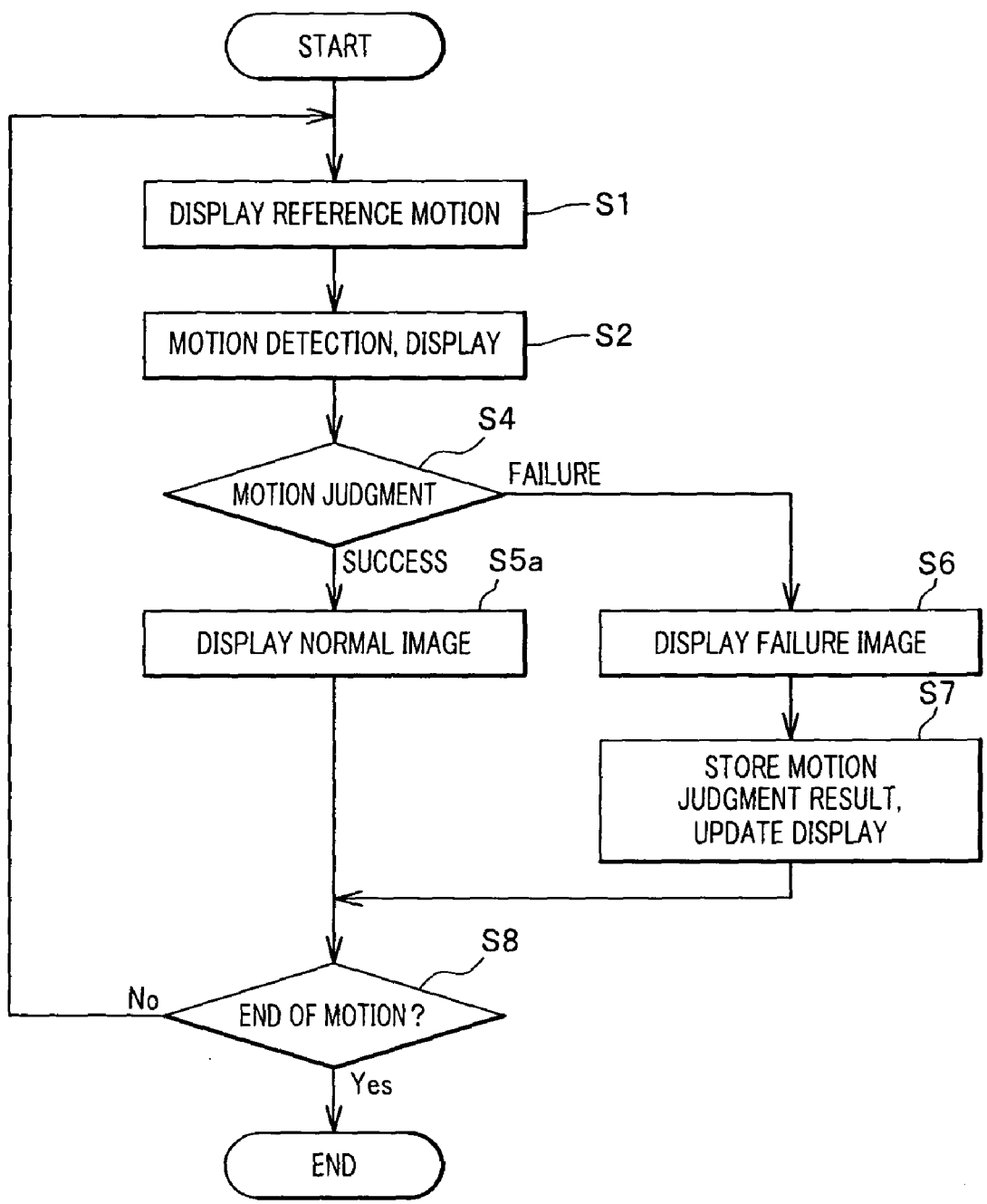
FIG. 9 is a flow chart showing processing of the controller 3 in the case that the image example 2 is displayed in the display means 4.

Next, the processing of controller 3 in the case that the image example 2 is displayed in the display means 4 will be described. FIG. 9 is a flow chart showing processing of controller 3 in the case that the image example 2 is displayed in the display means 4. Here, the case that the exerciser M practices training exercises of his or her legs for the number of predetermined times (for example, ten times) by using the training machine 1 shown in FIG. 2 is assumed.

The instruction output section 333 of the calculation unit 33 in the controller 3 instructs the display means 4 to display the reference motion (the meter indications 448) (step S1). The exerciser M practices training exercises of his or her legs while looking at the reference motion (the meter indications 448) in the display means 4.

The motion detection section 331 receives the detection signals from the input interface 31 and detects motion of the exerciser M (motion of the press part 13 in the training machine 1). The instruction output section 333 instructs the display means 4 to display motion of the own ship 442 by using the result of detection (step S2).

Next, the motion judgment section 332 does the motion judgment (step S4). Specifically, the motion judgment section 332 compares motion information of the exerciser detected by the motion detection section 331 and the reference motion information 321, and concludes that motion of the exerciser is normal (success) if the difference is smaller than the motion judgment threshold information 322, concludes that motion of the exerciser is failure if the difference is not smaller than the motion judgment threshold information 322.

If the result of the motion judgment is "normal" (step S4→"normal"), the instruction output section 333 instructs the display means 4 to display normal (success) image (step S5a: its detail will be described with reference to FIG. 10A). After it, processing of step S8 is performed.

If the result of the motion judgment is "failure" (step S4→"failure"), the instruction output section 333 instructs the display means 4 to display the failure image (step S6: its detail will be described with reference to FIG. 10B).

After FIG. 6, the storage instruction section of motion judgment result 334 instructs the storage unit 32 to store the result "failure" of motion judgment in step S4 as the motion judgment result information 323 and instructs the display means 4 to update the display (step S7).

Next, the motion detection section 331 judges whether motion of the training is over or not (step S8). The motion detection section 331 judges whether motion of the training is over or not, for example by judging whether the detection signals from the input interface 31 changes or not, or by judging whether the number of motion times of the training reaches the predetermined number of times (for example, ten times) or not.

If motion of the training is not over (step S8→No), the processing returns to step S1. If motion of the training is over (step S8→Yes), the processing is over.

Next, a normal (success) image example and a failure image example of training motion, as for second image example will be described. FIG. 10A is a normal image example, FIG. 10B, 10C are failure image examples.

An image that the own ship 442 doesn't contact both the guidance ship 443 and the rescue ship 444 is displayed for the normal image in the FIG. 10A (step S5a).

As shown in FIG. 10B, in a failure example 1, motion of the exerciser M is very slower than the reference motion. Therefore, the motion judgment section 332 compares motion information of exerciser detected by the motion detection section 331 and the reference motion information 321, and concludes that motion of the exerciser is failure because the difference is not smaller than the motion judgment threshold information 322 (step S4→>"failure").

Therefore, the instruction output section 333 instructs the display means 4 to display the failure image (step S6). In other words, the instruction output section 333 instructs the display means 4 to display an image in which the own ship 442 is in contact with the rescue ship 444 as the failure image. Then, the storage instruction section of motion judgment result 334 instructs the storage unit 32 to store the result "failure" of motion judgment in step S4 as the motion judgment result information 323 and instructs the display means 4 to display the number of failure times in the display area 431 after adding "1" to the number (step S7). In addition, in step S6, the display means 4 may display "Your motion is too slow" beside the rescue ship 444 in the display means 4 and the voice means 5 may output voice of the display at the same time.

As shown in FIG. 10 C, in a failure example 2, motion of the exerciser M is very faster than the reference motion. Therefore, the motion judgment section 332 compares motion information of the exerciser detected by the motion detection section 331 and the reference motion information 321, and concludes that motion of the exerciser is failure because the difference is not smaller than the motion judgment threshold information 322 (step S4→>"failure").

Therefore, the instruction output section 333 instructs the display means 4 to display the failure image (step S6). In other words, the instruction output section 333 instructs the display means 4 to display an image in which the own ship 442 is in contact with the rescue ship 444 as the failure image. Then, the storage instruction section of motion judgment result 334 instructs the storage unit 32 to store the result "failure" of motion judgment in step S4 as the motion judgment result information 323 and instructs the display means 4 to display the number of failure times in the display area 431 after adding "1" to the number (step S7). In addition, in step S6, the display means 4 may display "Your motion is too fast" beside the guidance ship 443 in the display means 4 and the voice means 5 may output voice of the display at the same time.

Thus, according to the training support system S, the controller 3 processes to display an image that the own ship 442 doesn't contact both the guidance ship 443 and the rescue ship 444 as the normal image, if motion of the exerciser M is the same (or almost same) as the reference motion. In addition, the controller 3 processes to display an image in which the own ship 442 is in contact with either of the guidance ship 443 or the rescue ship 444 as the failure image, and to add "1" to the number of failure times in the display area 431, if motion of the exerciser M doesn't is the same as the reference motion. Therefore, the exerciser M may practice training exercises with game sense, pleasure and high motivation, while performing safe and effective motion similar to the reference motion.

In addition, according to the training support system S, by connecting the training with sight information, not only the training of the muscle but also the training of the cooperation of the nerve and the muscle can be realized.

In addition, in FIG. 4 and FIG. 9, necessary processings for this invention are step S1 and S2 (its repetition). Because of this, the exerciser M may practice training exercises with game sense, pleasure and high motivation, while performing safe and effective motion similar to the reference motion by knowing visually the difference between motion of the exerciser M and the reference motion.

In addition, by the processing of other steps in FIG. 4 and FIG. 9 being performed more, the exerciser M may practice training exercises with higher motivation, because the exerciser M may make the ball 43 goes into the goal 44 in the image example 1, and the exerciser M may adjust speed (position) of the own ship 442 in the image example 2.

In addition, in the image example 2, display of position of the own ship 442 may be reset every one cycle of reciprocating motion, or may be processed cumulatively.

The explanation of the embodiment will be over. However, the state of this invention is not limited to these. For example, in the embodiment, the example of the case in which the servomotor 16 is used is described, but other means such as ball screw, rack & pinion, linear motor, board weights, oil pressure, spring, air resistance, water resistance may be used.

In addition, this invention is applied to the whole of the training machine with which the training is performed with a load, such as the leg press machine, a chest press machine and an arm curl machine. In addition, in the range that doesn't deviate from a purpose of this invention, concrete constitution may be changed.

What is claimed is:

1. A training support system comprising:
a display means for displaying training information on a training motion for a exerciser who uses a training machine for training of muscles; and
a controller;
wherein the controller comprises;
a reference motion setting section for setting a reference motion information on a reference motion, the reference motion information given to the exerciser by using at least one of speed information, time information, displacement information which are related to the training and are stored in a storage unit or are input from an input means;
a motion detection section for detecting the training motion of the exerciser by using detection signals from a sensor which detects the training motion; and
a instruction output section for making an image corresponding to the reference motion and an image corresponding to the training motion, and instructing the display means to display them dynamically;
wherein the controller makes the display means change the display depending on a difference between the reference motion and the training motion by judging whether the difference is within a predetermined range or not at a timing just before a turning point of a reciprocating motion on the training machine, and instructing the display means to display a success image if the difference is within the predetermined range.

2. The training support system according to claim 1,
when the controller makes the display means change the display depending on the difference,
the controller judges whether the difference is within the predetermined range or not, and instructs the display means to display a failure image if the difference is not within the predetermined range.

3. A training support method comprising:
a display means for displaying training motion information on a training motion for a exerciser who uses a training machine for training of muscles and a controller;
the method comprising the steps of:
the controller setting reference motion information on a reference motion, the reference motion information given to the exerciser by using a t least one of speed information, time information, displacement information which are related to the training motion and are stored in a storage unit or are input from an input means;
detecting the training motion of the exerciser by using detection signals from a sensor which detects the training motion; and
making an image corresponding to the reference motion and an image corresponding to the training motion, and instructing the display means to display them dynamically;
wherein the controller makes the display means change the display depending on a difference between the reference motion and the training motion by judging whether the difference is within a predetermined range or not at a timing just before a turning point of the reciprocating motion on the training machine, and instructing the display means to display a success image if the difference is within the predetermined range.

4. The training support method according to claim 3,
when the controller makes the display means change the display depending on the difference,
the controller judges whether the difference is within a predetermined range or not, and instructs the display means to display a failure image if the difference is not within the predetermined range.

* * * * *

UNITED STATES PATENT AND TRADEMARK OFFICE
CERTIFICATE OF CORRECTION

| | | |
|---|---|---|
| PATENT NO. | : 8,337,364 B2 | Page 1 of 1 |
| APPLICATION NO. | : 12/735859 | |
| DATED | : December 25, 2012 | |
| INVENTOR(S) | : Ishii et al. | |

It is certified that error appears in the above-identified patent and that said Letters Patent is hereby corrected as shown below:

Title Page should read:

(22) PCT Filed: Mar. 19, 2009

Signed and Sealed this
Fourteenth Day of May, 2013

Teresa Stanek Rea
*Acting Director of the United States Patent and Trademark Office*